United States Patent [19]

Lachnit-Fixson

[11] 3,939,264

[45] Feb. 17, 1976

[54] METHOD FOR CONTRACEPTION BY THE ADMINISTRATION OF SEQUENTIAL CONTRACEPTIVE PREPARATIONS

[75] Inventor: Ursula Lachnit-Fixson, Berlin, Germany

[73] Assignee: Schering Aktiengesellschaft, Berlin & Bergkamen, Germany

[22] Filed: Apr. 12, 1973

[21] Appl. No.: 350,590

[30] Foreign Application Priority Data

Apr. 14, 1972  Germany............................ 2218831
Mar. 3, 1973  Germany............................ 2310963

[52] U.S. Cl. ........... 424/239; 260/397.4; 260/397.5
[51] Int. Cl.² ...................... A61K 31/56; C07J 9/00
[58] Field of Search .................................... 424/239

[56] References Cited
UNITED STATES PATENTS

| | | | |
|---|---|---|---|
| 3,502,772 | 3/1970 | Ijzerman | 424/239 |
| 3,568,828 | 3/1971 | Lerner | 424/239 |
| 3,639,600 | 2/1972 | Hendrik | 424/243 |
| 3,733,407 | 5/1973 | Segre | 424/239 |
| 3,795,734 | 10/1974 | Rochefort | 424/242 |

Primary Examiner—Elbert L. Roberts
Attorney, Agent, or Firm—Millen, Raptes & White

[57] ABSTRACT

Oral contraceptive consisting essentially in admixture with a pharmaceutically acceptable carrier, of 21–23 separate dosage units adapted for oral ingestion, containing an amount of an estrogen corresponding in activity to 0.030–0.050 mg. 17$\alpha$-ethinylestradiol, with the first 10–12 dosage units being in combination with a gestagen corresponding in activity to about 0.050–0.125 mg. of d-norgestrel and the remainder in combination with a gestagen corresponding in activity to 2–3 times the amount of gestagen in the first 10–12 units.

6 Claims, No Drawings

METHOD FOR CONTRACEPTION BY THE ADMINISTRATION OF SEQUENTIAL CONTRACEPTIVE PREPARATIONS

BACKGROUND OF THE INVENTION

Numerous hormonal methods for contraception are known, i.e., the oral administration of combination-type preparations, e.g. "Ovulen", "Anovlar", "Lyndiol", and similar combinations of estrogenic and gestagenic active agents. Also conventional is the administration of purely sequential preparations, such as, for example, "Ovanone", etc., wherein first an estrogen is administered at a high dosage in the absence of gestagen, over a period of 7 days, and thereafter the estrogene is administered at the same high dosage in combination with a relatively high amount of gestagen over a period of 15 days, with the next 6 days being a blank period without administration of estrogenic or gestagenic agent in order to mimic the normal 28-day menstrual cycle of the woman.

The administration of modified sequential preparations is likewise conventional, such as, for example, "Kombiquens", "Tri-Ervonum", and "Oraconal", etc., wherein first an estrogen is administered at a high dosage in combination with a low amount of gestagen over a period of 16 days, and subsequently the estrogen is administered over a period of about 7 days at the same high dosage in combination with an amount of gestagen about 5–10 times the original amount. See U.S. Pat. No. 3,568,828. To adapt to the natural 28-day cycle of the female, a 5-day hormone-free period follows the administration of these preparations wherein placebos or any desired other non-contraceptive effective agents are taken, such as, for example, tonics, iron supplements, etc.

The disadvantages of the administration of the above-mentioned sequential preparations are, in particular, the relatively high doses of estrogen, resulting, in addition to evoking the customary symptoms caused by an excess of estrogen, such as, for example, gastrointestinal disturbances, nausea, weight gain from edema, etc., along with an increase in the risk of thromboembolism. On the other hand, however, it was considered essential to ingest high doses of estrogen for reliable contraceptive effect.

SUMMARY OF THE INVENTION

According to this invention, reliable contraception is attained by administering orally an estrogen at a low dosage for about 21–23 days, first in combination with a gestagen at a low dosage for a period of 10–12 days and thereafter in combination with a gestagen at a dosage 2 to 3 times as great, for the next 11–9 days. For adaption to the normal female 28-day menstrual cycle, no estrogens and gestagens are administered for the subsequent 7–5 days, for a total of about 28 days. This latter phase can be without administration of any drug in a conventional manner, or placebos or a non-contraceptive active agent can be administered without adverse effect on the method.

In its composition aspect, this invention relates to a two-stage oral contraceptive composition consisting essentially of about 21–23 separate dosage units adapted for successive daily oral ingestion and containing in admixture with a pharmaceutically acceptable carrier an estrogen at a low dosage, of which the first 10–12 dosage units are in combination with a gestagen at a low dosage, and the next 11–9 dosage units are in combination with a gestagen at a dosage 2–3 times as high, and any remainder being free of estrogenic and gestagenic agents.

DETAILED DISCUSSION

By the method of this invention, it is possible to administer low dosages of estrogen which is strongly recommended by the medical profession, by the sequential principle. On the other hand, by increasing the amount of gestagen in the middle of the period of administration, the course of the normal cycle, i.e., the normal physiological activities, are imitated. By this quasi-adaption to the physiological cycle, an improved compatibility of the preparations is obtained, and an optimum control is exerted over the cycle.

Suitable estrogen components for the method of this invention for contraception are the known estrogens. In this connection, the estrogen employed should be administered in such dosages that the amount of estrogen utilized according to this invention is equal to that corresponding to 0.030–0.050 mg. of 17α-ethinylestradiol, as measured in conventional tests, c. J. Ufer, Hormontherapie in der Frauenheilkunde, De Gruyter Verlag Berlin-New York, 1972, 4. Auflage, P. 27. 17α-Ethinylestradiol esters and ethers, as well as the estradiol esters are suitable as the estrogen component. 17α-Ethinylestradiol is preferred.

The gestagen (progestagen) employed according to this invention in combination with the estrogen, can be the same or preferably different in the first and second stages. When different gestagens are utilized in the first and second stages, the instant method, in addition to the above-described advantages, has the further advantage that the side-effects of a specific gestagen are reduced or eliminated by administering this gestagen in one stage while another gestagen, which has a competitive behavior with respect to the side-effects, is administered in the other stage. Thus, it is possible, for example, to use the estrogen in one stage in combination with a gestagen derived from testosterone or 19-nortestosterone which optionally has a substituted hydrocarbon residue in the 17α-position. These (19-nor-) testosterone derivatives generally exhibit a minor androgenic side effect. In the other stage, the estrogen can then be employed in combination with a gestagen derived from progesterone which does not exhibit the androgenic side effect inherent in such testosterone or 19-nortestosterone derivatives. Those progesterone derivatives are considered especially advantageous which, in addition to the gestagenic activity, have antiandrogenic side effects.

When using different gestagens in the first and second stages, a preferred embodiment employs, in the first stage, the estrogen in combination with a testosterone or 19-nortestosterone derivative as the gestagen component and, in the second stage, the estrogen in combination with a progesterone derivative as the gestagen component.

Suitable as the gestagen component according to the present invention are all substances having significant gestagenic activity. In this connection, the gestagen employed should be administered at such dosages that the amount of gestagen utilized in the first 10–12 days according to this invention corresponds to 0.050–0.125 mg. daily of d-norgestrel as measured in the conventional tests, c. J. Ufer, Hormontherapie in der Frauenheilkunde, De Gruyter Verlag Berlin-New York 1972, 4. Auglage, p. 28.

The amount of gestagen employed according to this invention in the 11–9 days of the second phase is about 2–3 times that employed in the first phase, i.e., corresponds in activity to about 0.100–0.350 mg. daily of d-norgestrel.

Examples of suitable gestagen components are progesterone and the derivatives thereof, such as, for example, 17-hydroxyprogesterone esters and 19-nor-17-hydroxyprogesterone esters and the derivatives thereof, or 18-methyl homologs. Derivatives are compounds having progestational activity formed by the introduction of a double bond or double bonds into the molecule by substitution, or by the production of functional derivatives, such as, for example, esters, ethers, ketals, etc. As mentioned above, other suitable gestagens are testosterone or 19-nortestosterone derivatives, such as, for example, 17α-ethinyl-19-nortestosterone, the 18-methyl homologs thereof, as well as functional derivatives, such as, e.g., esters or ethers. For other examples, see those employed in the oral contraceptives listed in *Physicians' Desk Reference*, 1973 Edition.

The double bonds in the progesterone derivatives can be present, inter alia, in the 1(2)-, 6(7)- and/or 16(17)-position. Suitable substituents are, inter alia, halogen, especially fluorine, chlorine, and bromine atoms, lower alkyl, especially the methyl group, alkenyl, alkinyl, especially the ethinyl group, and/or the hydroxy group, all of which can be in the 4-, 6-, 7-, 16- and/or 17-position, as well as methylene groups, which can be in the 1(2)-, 6(7)- and/or 16(17)-position. Suitable esters are the esters of acids customarily employed in the steroid chemistry for the esterification of the steroid alcohols. Examples in this connection are alkanecarboxylic acids, especially alkanecarboxylic acids of 1–7 carbon atoms. Examples for suitable ethers are alkyl and tetrahydropyranyl ethers. Suitable ketals are, for example, those of ethanediol or those of the propanediols.

Preferred gestagens, which are testosterone derivatives, are d-norgestrel and 17α-ethinyl-19-nortestosterone acetate. Examples of preferred gestagens which are progesterone derivatives are 6-chloro-1,2α-methylene-4,6-pregnadien-17α-ol-3,20-dione 17-acetate (cyproterone acetate) and 6-chloro-1,2α-methylene-4,6-pregnadien-16α-methyl-17α-ol -3,20-dione 17-acetate.

The estrogenic and gestagenic agents are preferably administered orally, but can also be administered separately or parenterally. For this purpose, the effective agents are processed according to conventional methods into the customary forms of application, together with the additives, vehicles and/or flavor-ameliorating agents used in galenic pharmacy. Especially suitable for the preferred oral administration are tablets, dragees, capsules, pills, suspensions, or solutions, and for parenteral application, in particular, oily solutions, such as, for example, sesame oil or castor oil solutions which can optionally contain additionally a diluent, such as, e.g., benzyl benzoate or benzyl alcohol.

The oral contraceptive compositions adapted for oral ingestion are provided as a packaged sequence of unit dosage forms adapted for oral ingestion of one unit dosage form daily in sequence for 19–23 days, preferably 21 days, preferably followed in sequence by about 5–7 placebos to provide a total of 28 unit dosages per package. The unit dosages are preferably packaged in the conventional bubble plastic package having 28 bubbles in a sheet of flexible plastic arranged in an oval or circle, each containing a unit dosage with the placebos being positioned so as to be ingested last. The bubbles are sealed by a tangible sheet which is adapted to break and release the unit dosage when the bubble is pressed.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

(Composition of a Dragee, per Stage)

| First Stage: | 0.050 mg. | 17 α-Ethinylestradiol |
|---|---|---|
| | 0.050 mg. | d-Norgestrel |
| | 33.150 mg. | Lactose |
| | 18.000 mg. | Corn Starch |
| | 2.100 mg. | Polyvinylpyrrolidone |
| | 1.650 mg. | Talc |
| | 55.000 mg. | Total weight, which is supplemented to about 90 mg. with the usual sugar mixture. |
| Second Stage: | 0.050 mg. | 17α-Ethinylestradiol |
| | 0.125 mg. | d-Norgestrel |
| | 33.075 mg. | Lactose |
| | 18.000 mg. | Corn starch |
| | 2.100 mg. | Polyvinylpyrrolidone |
| | 1.650 mg. | Talc |
| | 55.000 mg. | Total weight, which is supplemented to about 90 mg. with the usual sugar mixture. |

EAMPLE 2

(Composition of a Tablet, per Stage)

| First Stage: | 0.050 mg. | 17α-Ethinylestradiol |
|---|---|---|
| | 1.000 mg. | 17α-Ethinyl-19-nortestosterone acetate |
| | 32.100 mg. | Lactose |
| | 18.000 mg. | Corn starch |
| | 2.100 mg. | Polyvinylpyrrolidone |
| | 1.650 mg. | Talc |
| | 0.100 mg. | Magnesium stearate |
| | 55.000 mg. | Total weight, which is supplemented to about 90 mg. with the usual sugar mixture. |
| Second Stage: | 0.050 mg. | 17α-Ethinylestradiol |
| | 2.000 mg. | 17α-Ethinyl-19-nor-testosterone acetate |
| | 31.100 mg. | Lactose |
| | 18.000 mg. | Corn starch |
| | 2.100 mg. | Polyvinylpyrrolidone |
| | 1.650 mg. | Talc |
| | 0.100 mg | Magnesium stearate |
| | 55.000 mg. | Total weight, which is supplemented to about 90 mg. with the usual sugar mixture. |

EXAMPLE 3

(Composition of a Tablet, per Stage)

| First Stage: | 0.050 mg. | 17α-Ethinylestradiol |
|---|---|---|
| | 1.000 mg. | 17α-Ethinyl-19-nor-testosterone acetate |
| | 32.100 mg. | Lactose |
| | 18.000 mg. | Corn Starch |
| | 2.100 mg. | Polyvinylpyrrolidone |
| | 1.650 mg. | Talc |
| | 0.100 mg. | Magnesium stearate |
| | 55.000 mg. | Total weight, which is supplemented to about 90 mg. with the usual sugar mixture. |
| Second Stage: | 0.050 mg. | 17α-Ethinylestradiol |
| | 2.000 mg. | Cyproterone acetate |
| | 31.100 mg. | Lactose |
| | 18.000 mg. | Corn starch |

-continued (Composition of a Tablet, per Stage)

| | |
|---|---|
| 2.100 mg. | Polyvinylpyrrolidone |
| 1.650 mg. | Talc |
| 0.100 mg. | Magnesium stearate |
| 55.000 mg. | Total weight, which is supplemented to about 90 mg. with the usual sugar mixture. |

TABLE 1-continued

| Age in Years | Number of Patients | |
|---|---|---|
| | Absolute | Percent |
| 26–30 | 76 | 29.9 |
| 31–35 | 49 | 19.3 |
| 36–40 | 40 | 15.7 |
| 41–45 | 17 | 6.7 |
| 46–50 | 2 | 0.8 |
| Above 50 | — | — |
| Subtotal | 253 | 99.6 |
| No data | 1 | 0.4 |
| Total | 254 | 100 |

TABLE 2

COMPARISON

| Intermediate Bleeding Prior to Treatment % | Spot Bleeding Last Untreated Cycle % | Spot Bleeding First Cycle (254 Women) % | Bleeding Between Periods First Cycle (254 Women) % |
|---|---|---|---|
| 5.9 | 18.9 | 10.6 | 4.0 |

| | Spot Bleeding Total Number of Treatment Cycles (1,441) % | Bleeding Between Periods Total Number of Treatment Cycles (1,441) % |
|---|---|---|
| | 8.1 | 2.4 |

EXAMPLE 4

(Composition of a Dragee, per Stage)

| First Stage: | 0.050 mg. | 17α-Ethinylestradiol |
|---|---|---|
| | 0.075 mg. | d-Norgestrel |
| | 33.125 mg. | Lactose |
| | 18.000 mg. | Corn starch |
| | 2.100 mg. | Polyvinylpyrrolidone |
| | 1.650 mg. | Talc |
| | 55.000 mg. | Total weight, which is supplemented to about 90 mg. with the usual sugar mixture. |
| Second Stage: | 0.050 mg. | 17α-Ethinylestradiol |
| | 0.200 mg. | 6-Chloro-1,2α-methylene-16α-methyl-4,6-pregnodien-17α-ol-3,20-dione 17-acetate |
| | 33.050 mg. | Lactose |
| | 18.000 mg. | Corn starch |
| | 2.100 mg. | Polyvinylpyrrolidone |
| | 1.600 mg. | Talc |
| | 55.000 mg. | Total weight, which is supplemented to about 90 mg. with the usual sugar mixture. |

TABLE 3

COMPARISON

| Side Effects | Last Untreated Cycle (254 Women) % | Total Number of Treatment Cycles (1,441) % |
|---|---|---|
| Dysmenorrhea | 7.9 | 1.8 |
| Nausea and vomiting | 6.3 | 5.7 |
| Dizziness | 4.7 | 1.3 |
| Other symptoms | 7.5 | 6.7 |
| Tenderness of the breasts | 7.9 | 6.8 |
| Headaches | 13.8 | 8.2 |
| Nervousness | 14.2 | 6.3 |
| Depressions | 6.3 | 3.5 |
| Reduction of libido | 13.4 | 8.8 |
| Acne | 4.0 | 1.3 |
| Chloasma | 0.4 | 0.4 |
| Edemas | 0.4 | 0.2 |
| Varices | 3.2 | 1.8 |
| Thrombophlebitis | — | — |
| Hepatopathy | — | 0.1 |

Clinical Tests

EXAMPLE 5

A preparation according to Example 1 was administered to 254 women in the child-bearing age (Table 1) daily for 11 days (first stage) and daily for the following 10 days (second stage) per woman; the subsequent 7 days, during which the menstrual bleeding occurred, remained without administration. This regimen of administration (11 days/first stage and 10 days/second stage and 7 days/blank) was maintained for most of the women for up to 6 months, thus resulting in a total number of 1,441 treatment cycles.

During the entire treatment period, no pregnancies occurred. The preparation was of excellent compatibility; the number of intermediate and spot bleeding was considerably reduced as compared to these occurrences prior to treatment (Table 2); the side effects were likewise, in part, markedly reduced as compared to the last cycle prior to treatment (Table 3).

TABLE 1

| Age in Years | Number of Patients | |
|---|---|---|
| | Absolute | Percent |
| Up to 20 | 10 | 4.0 |
| 21–25 | 59 | 32.2 |

EXAMPLE 6

493 Women in the child-bearing age (Table 4) received daily for 11 days (first stage) and daily for the following 10 days (second stage) per woman a preparation according to Example 2; the subsequent 7 days, during which the menstrual bleeding occurred, remained without administration. This regimen of administration (11 days/first stage and 10 days/second stage and 7 days/blank) was maintained for most of the women for up to 6 months, resulting in a total number of 2,544 treatment cycles.

No pregnancies occurred during the entire treatment period. The preparation exhibited excellent compatibility; a favorable influence was exerted on the number of intermediate bleedings and spottings as compared to the number prior to treatment. Also, the side effects were likewise, in part, markedly reduced as compared to the last cycle prior to treatment.

TABLE 4

| Age in Years | Number of Patients | Percent of Total |
|---|---|---|
| 15–20 | 155 | 31.7 |
| 21–25 | 141 | 28.8 |
| 26–30 | 69 | 14.1 |

TABLE 4-continued

| Age in Years | Number of Patients | Percent of Total |
|---|---|---|
| 31–35 | 63 | 12.9 |
| 36–40 | 38 | 7.8 |
| 41–45 | 20 | 4.1 |
| 46–50 | 3 | 0.6 |
| Subtotal | 489 | 99.2 |
| No data | 4 | 0.8 |
| Total | 493 | 100 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of oral contraception which comprises administering orally to a female of child-bearing age an estrogen at a daily dosage of 0.050 mg. of 17α-ethinylestradiol for 21 days of her menstrual cycle, either (a) in combination the first 11 days with 0.050 mg. per day of d-norgestrel followed for the next 10 days by 0.125 mg. per day of d-norgestrel, or (b) in combination the first 11 days with 1 mg. of 17α-ethinyl-19-nortestosterone acetate followed for the next 10 days by 2 mg. per day of 17α-ethinyl-19-nortestosterone acetate.

2. The method of claim 1 employing the combination of 17α-ethinylestradiol and d-norgestrel.

3. The method of claim 1 employing the combination of 17α-ethinylestradiol and 17α-ethinyl-19-nortestosterone acetate.

4. A two-stage combination oral contraceptive composition consisting essentially of 21 separate dosage units adapted for successive daily oral ingestion and each containing in admixture with a pharmaceutically acceptable carrier, 0.050 mg. of 17α-ethinylestradiol and either (a) 0.050 mg. of d-norgestrel in the first 11 dosage units and 0.125 mg. of d-norgestrel in the next 10 dosage units, or (b) 1 mg. of 17α-ethinyl-19-nortestosterone acetate in the first 11 dosage units and 2 mg. of 17α-ethinyl-19-nortestosterone acetate in the next 10 dosage units, any other dosage units being free of estrogenic and gestagenic agents.

5. The two-stage combination of claim 4 wherein the 17α-ethinylestradiol is in combination with d-norgestrel.

6. The two-stage combination of claim 4 wherein the 17α-ethinylestradiol is in combination with 17α-ethinyl-19-nortestosterone acetate.

* * * * *